(12) United States Patent
Muhlsteff et al.

(10) Patent No.: US 8,233,969 B2
(45) Date of Patent: Jul. 31, 2012

(54) WEARABLE MONITORING SYSTEM

(75) Inventors: Jens Muhlsteff, Aachen (DE); Jeroen Adrianus Johannes Thijs, Aachen (DE)

(73) Assignee: Koninklijke Philips Electronics, N.V., Eindhoven (NL)

( * ) Notice: Subject to any disclaimer, the term of this patent is extended or adjusted under 35 U.S.C. 154(b) by 269 days.

(21) Appl. No.: 12/306,000

(22) PCT Filed: Jun. 28, 2007

(86) PCT No.: PCT/IB2007/052512
§ 371 (c)(1),
(2), (4) Date: Dec. 22, 2008

(87) PCT Pub. No.: WO2008/004159
PCT Pub. Date: Jan. 10, 2008

(65) Prior Publication Data
US 2009/0204013 A1    Aug. 13, 2009

(30) Foreign Application Priority Data

Jul. 5, 2006  (EP) ................................. 06116624
Jul. 11, 2006  (EP) ................................. 06116930

(51) Int. Cl.
*A61B 5/04*    (2006.01)
(52) U.S. Cl. ......................................................... 600/509

(58) Field of Classification Search .................. 600/388, 600/509, 513
See application file for complete search history.

(56) References Cited

U.S. PATENT DOCUMENTS

| | | | |
|---|---|---|---|
| 3,835,840 A | | 9/1974 | Mount |
| 4,016,868 A | * | 4/1977 | Allison ........................ 600/388 |
| 6,047,203 A | * | 4/2000 | Sackner et al. .............. 600/388 |
| 7,029,447 B2 | * | 4/2006 | Rantala ....................... 600/485 |
| 2002/0032386 A1 | | 3/2002 | Sackner et al. |

FOREIGN PATENT DOCUMENTS

| | | |
|---|---|---|
| GB | 2143135 A | 2/1985 |
| JP | 2001299712 A | 10/2001 |
| JP | 2001340311 A | 12/2001 |
| WO | 03075693 A1 | 9/2003 |
| WO | 03082103 A1 | 10/2003 |
| WO | WO 03/082103 A  * | 10/2003 |
| WO | 2004045405 A1 | 6/2004 |
| WO | 2005032365 A1 | 4/2005 |
| WO | 2006038235 A2 | 4/2006 |

\* cited by examiner

*Primary Examiner* — Niketa Patel
*Assistant Examiner* — Mallika Fairchild
(74) *Attorney, Agent, or Firm* — Michael W. Haas (57) ABSTRACT

A system for measuring/monitoring the vital signs of a patient especially blood pressure, comprising a plurality of electrodes arranged at least in the waistband of an undergarment, and means for deriving measurements from the electrodes using pulse-transit times.

14 Claims, 7 Drawing Sheets

Boxershort with integrated dry electrodes

WEARABLE MONITORING SYSTEM

BACKGROUND

1. Field of the Invention

This invention relates to monitoring systems adapted for continuously or at least regularly monitoring the vital signs of a subject, and particularly to a system for measuring blood pressure.

2. Description of Related Art

In all developed countries, cardio-vascular diseases like myocardial infarction, congestive heart failure or hypertension have an increasing impact on mortality and morbidity. There is an increasing demand for long term continuous monitoring of a patient's vital signs, which offers the opportunity to evaluate the performance of the cardio-vascular system. Various different blood pressure measurement systems have commonly been used in the past, which require a pressurized cuff or similar device which must be specially attached to the patient when a measurement is to be taken, and also require a suitably skilled clinician to operate them. Consequently such devices are usually confined to uses in a doctor's premises or in hospital, for example, and are not adapted for continuous or regular monitoring purposes.

SUMMARY

Accordingly the present invention seeks to provide a blood pressure measuring system, which utilizes Pulse Transit Time methodology for deriving measurements from detected signals such as the ECG, and can also be used for monitoring other vital signs. It is particularly suitable for implementation in a continuously wearable undergarment with integrated measuring sensors or electrodes, so as to be directly in contact with the subject's skin. Thus the present invention provides a system for measuring/monitoring the vital signs of a patient especially blood pressure, comprising a plurality of electrodes arranged at least in the waistband of an undergarment, and means for deriving measurements from the electrodes using pulse-transit times characterized in that the undergarment comprises a pair of underpants, having additional electrodes positioned in the leg portions so as to measure passing pulses in the left and right femoralis. In and exemplary embodiment, the garment includes at least four electrodes in order to allow PTT measurements to be made without additional connections to the patient's body.

In and exemplary embodiment, the sensors are of a type which do not require special attachment systems, gels or pastes to make proper electrical contact, for example they may be dry electrodes of a type recently developed, made from conductive rubber, which rely only on naturally-produced sweat to make a conductive bridge between the skin and the electrode.

In and exemplary embodiment, electrodes are so arranged as to measure the passing of pulses of the central artery, and the left and right femoralis, as well as the ECG. The system may also be arranged to monitor the temperature, the posture and the level of activity of the subject.

In and exemplary embodiment, pulse detection is achieved using bio-impedance methodology, by injecting a small AC current using a first pair of electrodes, and detecting voltage changes caused by the injected current, with a second pair of electrodes so as to produce an impedance plethysmogram. The exemplary arrangement of the electrodes is such that it is possible to measure the plethysmogram of the central aorta, as well as the left and right femoralis. At the same time, it is also possible to measure the ECG, using the dry electrodes in the waistband.

Some embodiments of the invention will now be described by way of example, with reference to the accompanying drawings, in which:

DETAILED DESCRIPTION OF EXEMPLARY EMBODIMENTS

The present invention proposes to use pulse wave velocity methodology, as a means of measuring vital parameters.

Pulse wave velocity (PWV) methodology is a suitable approach for monitoring mechanical parameters, but requires a set of at least two sensors distributed around the body. For instance recent research has confirmed a good correlation between the blood pressure BP and the velocity of pulse wave (PWV). After calibration e.g. via a blood pressure reference measurement with a cuff this technique allows a beat-to-beat determination of BP. Typically a relation of blood pressure and PWV in arteries is expressed by the Moens-Korteweg-relation, which can be derived from hydrodynamic theory:

$$c = \sqrt{\frac{hE_t}{2\rho R}}$$

Equation 1: Moens-Korteweg-equation often used to describe the relation of pulse-wave-velocity and blood pressure where: c=pulse wave velocity, $E_t$=tangential elasticity module, $\rho$=density, R=radius of artery, h=artery wall thickness.

The experimentally verified relation:

$$E = E_0 e^{\alpha P}, \alpha \approx 0.017 \text{ mmHg}^{-1}$$

Provides the link between the PWV and blood pressure (P) variations. The calibration step is necessary to scale the PWV to BP conversion, the other parameters ($\alpha$, $E_0$, h, r) being clearly subject-dependent and quite difficult to measure directly.

The PWV can be determined by measuring the time of a pressure wave travelling a certain distance in the arterial system in various ways (this time will be called pulse transit time PTT) e.g.:

1. The time-difference of a pulse passing two points at a distance d.

2. The time-difference between the R-peak in ECG-signal and a passing pulse in an artery at a certain body position.

Typical set-ups in the literature are:

1. ECG—and Photoplethysmography PPG; PTT is given by time-difference between R-peak and characteristic points in PPG. The PPG can be measured at various positions on the body e.g. ear or finger.

2. ECG and bio-impedance measurement at arm (impedance plethysmography IPG); PTT is given by the time-difference between R-peak and characteristic points in the IPG.

3. Impedance Cardiography (ICG) of the thorax and bio-impedance measurement at arm (IPG); PTT is given by the time-difference between characteristic points in the ICG and characteristic points in the IPG.

4. Impedance plethysmogram (IPG1) at a first position on an arm and bio-impedance measurement at a second position on an arm (IPG2); PTT is given by the time-difference between characteristic points in the IPG1 and characteristic points in the IPG2.

If clinical standard sensors or methodologies are used, all these methods have several disadvantages especially for Personal Healthcare applications. State of the art sensors such as finger or ear sensors measuring a photoplethysmogram or bio-impedance methodologies are rather an inconvenience in normal life requiring finger and ear PPG sensors or special medical electrodes, which must be glued to the skin. Therefore such state-of-the-art sensors are not suitable for long term continuous monitoring in Personal Healthcare applications.

Figure 2:
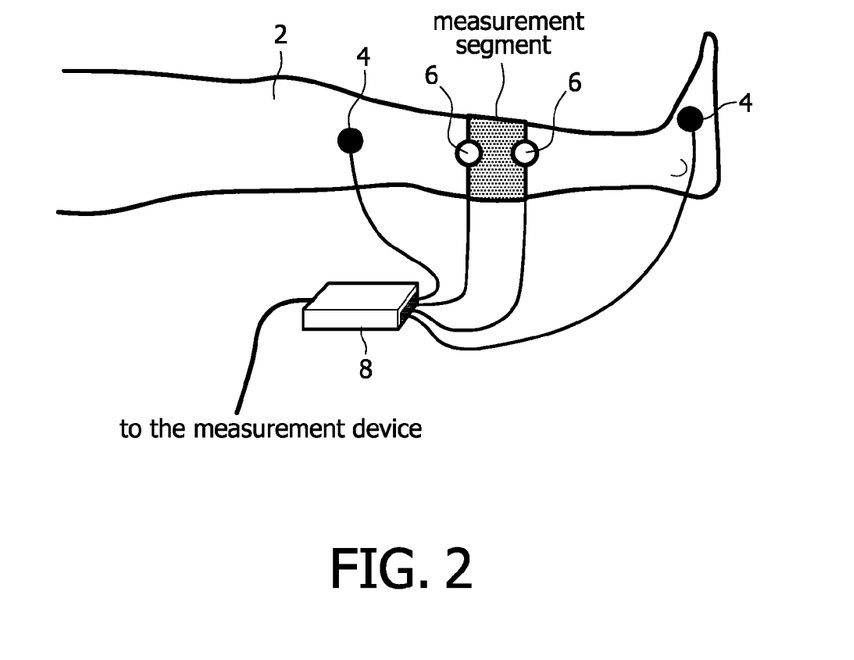
FIG. 2 illustrates a typical electrode arrangement for impedance plethysmography.

The general principle of bio-impedance measurements is illustrated by the diagram of FIG. 2, which shows the technique applied to the leg 2 of a patient, in which a small AC current is passed through it via a first pair of electrodes 4. The exciting current is a constant high frequency AC current with a very low amplitude (about 1 milliamp), which is therefore imperceptible to the patient, and does not have any significant physiological effects.

A further pair of electrodes 6 are then used to detect voltage changes caused by the exciting current, which are a measure of the variation in impedance caused by changes in blood volume and velocity. This enables the arterial volume pulsation to be measured, via a control/measuring circuit 8.

Figure 1:
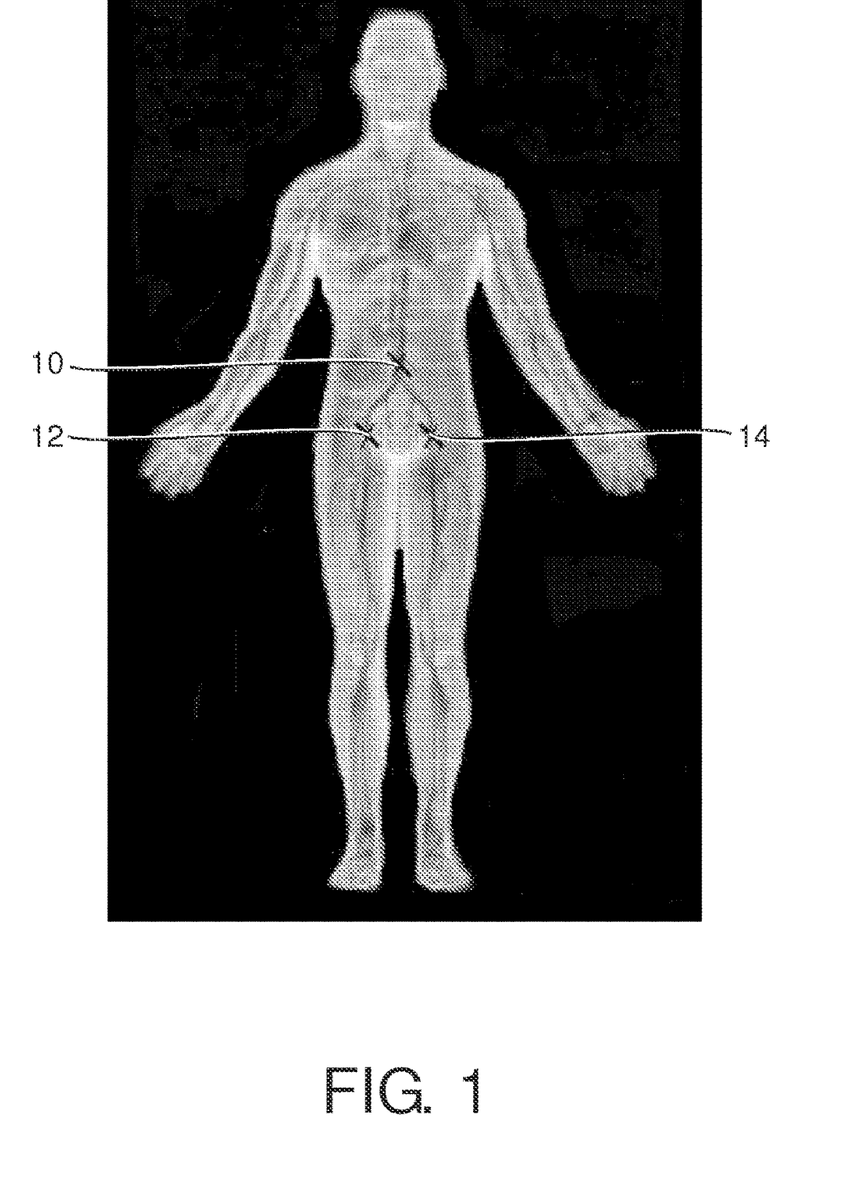
FIG. 1 is a diagrammatic view showing the main arteries in a human body.

It will be appreciated that the same principle can be applied to measurements made in other regions of the body, and the present invention therefore proposes to make measurements in the region of the subject's waist, as indicated at 10 in the schematic of FIG. 1, and also at 12 and 14 at the right and left femoralis, since these positions represent the major branching point of the subject's arterial system. The waistband position also has the significant advantage that a reasonably close fit of the electrodes in this region, will more naturally be accepted by the subject, since it corresponds to the normal position of the waistband of a garment. It is also significantly closer to the patient's heart, for making ECG measurements, and less subject to hydrostatic effects and motion artifacts than other possible monitoring sites for example in the limbs.

Figure 3:
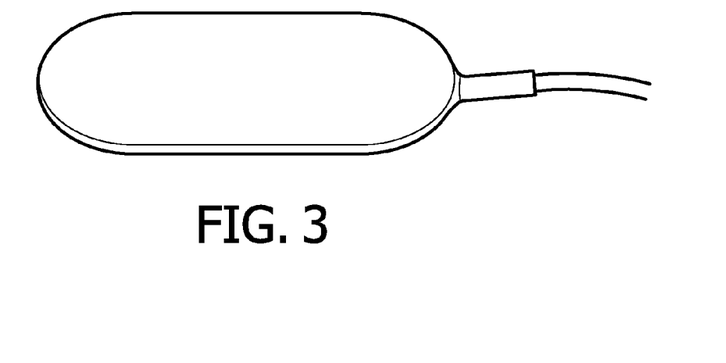
FIG. 3 shows a dry electrode of conductive rubber.

FIG. 3 illustrates a dry electrode made of conductive rubber, which has a flexible body and is therefore ideal for integrating into an item of clothing. In the exemplary arrangement of the invention, electrodes of this kind are integrated into an undergarment, such as the underpants 16 illustrated in FIG. 4, where a number of such electrode are fixed into the waistband, as indicated at positions 18. These electrodes are adapted to make good electrical contact to the wearer's skin, without requiring any special paste or glue, but simply by utilizing the conductivity of naturally secreted sweat. As is also shown in this Figure, a signal-processing circuit 20, corresponding to circuit 8 illustrated in FIG. 2, can also be integrated into the waistband of the garment, behind a zip pocket as illustrated at 20.

Figure 4:
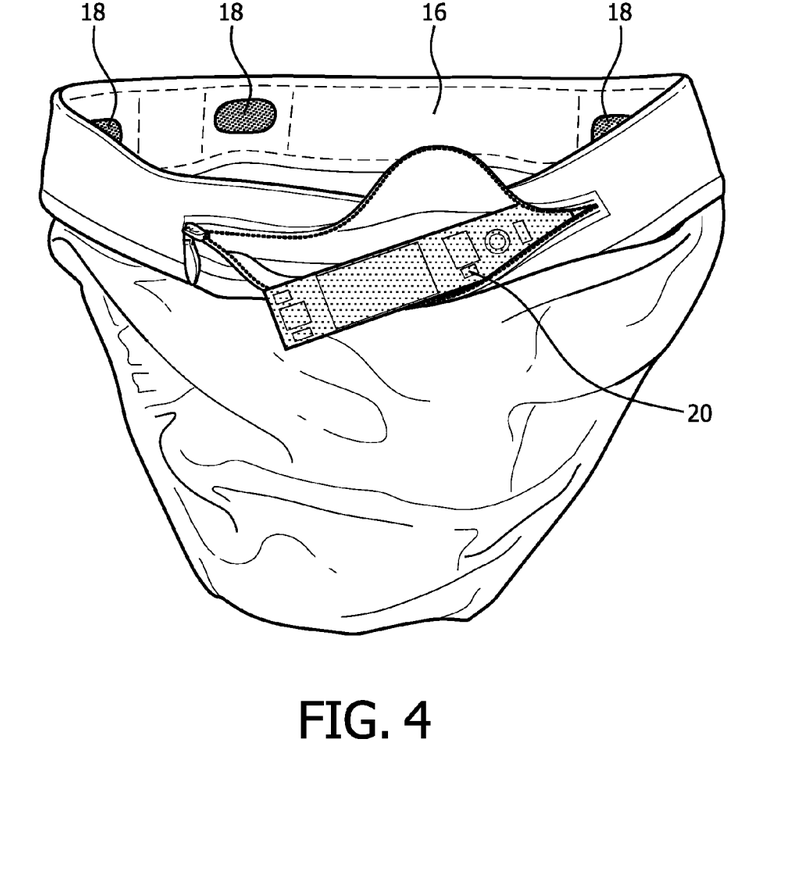
FIG. 4 illustrates an undergarment with integrated dry electrodes.
Figure 5:
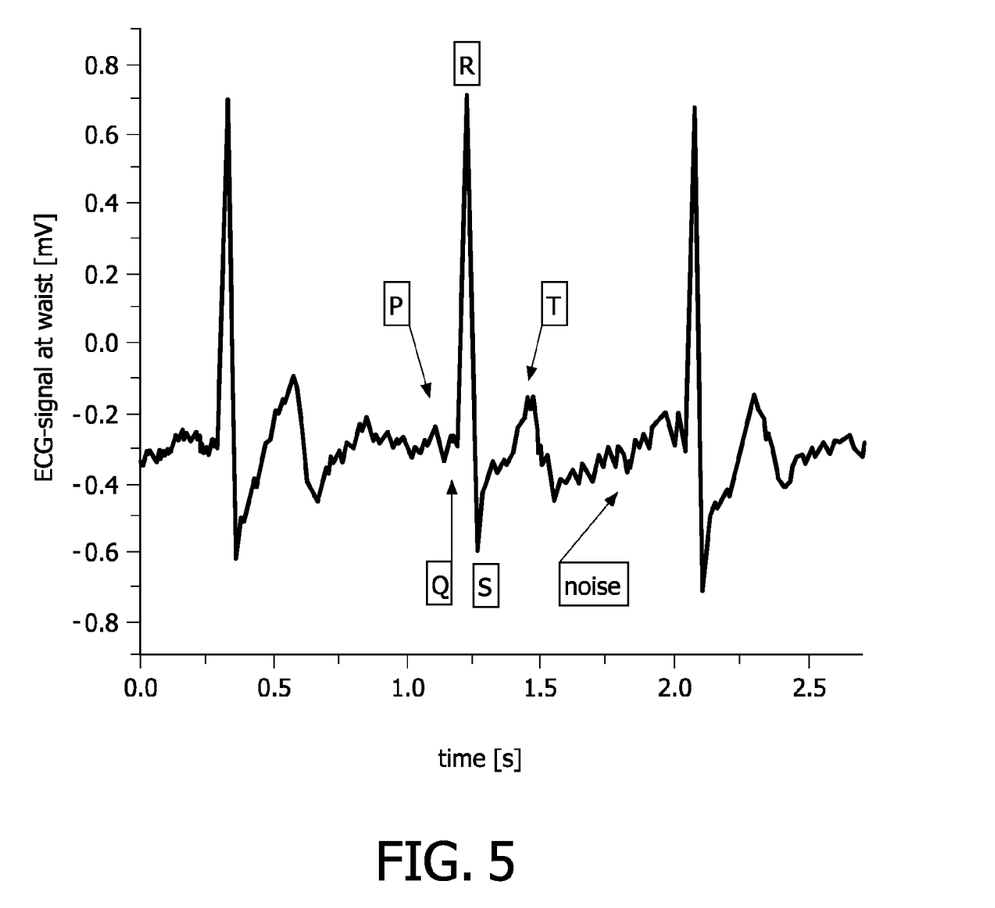
FIG. 5 illustrates an ECG signal measured at the waist.

FIG. 5 illustrates a typical ECG of a subject at rest, measured with the electrode arrangement of FIG. 4, in which the electrode positions are adjacent to the patient's hips, so that they are relatively well spaced apart and thus enclose a reasonably significant volume of the subject's body. It can be seen that all of the significant regions, i.e. the P-wave, the QRS complex, and the T-wave are clearly delineated in the signal.

Figure 6:
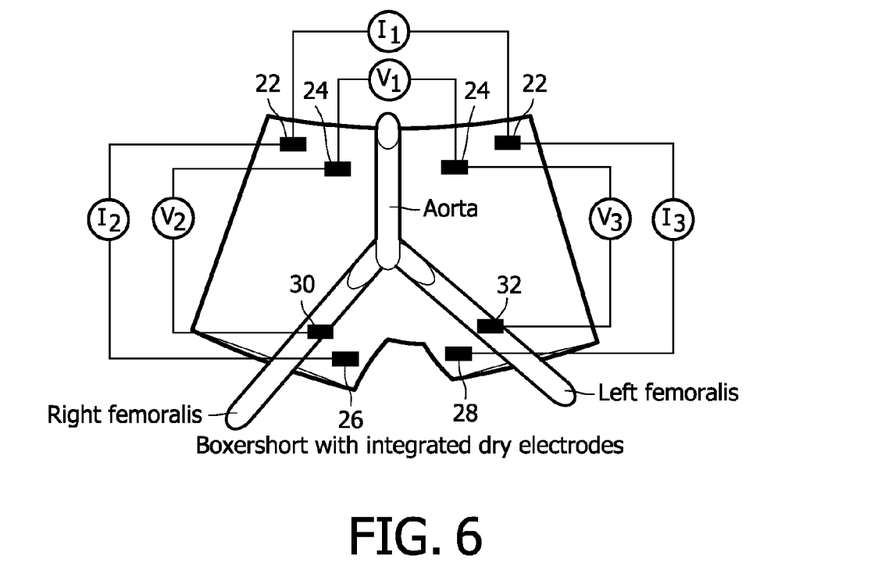
FIG. 6 illustrates diagrammatically, the relative position of integrated dry electrodes in an undergarment, and the relevant measurement regions.

FIG. 6 illustrates in a diagrammatic form, the different regions where a suitable undergarment may have integrated electrodes, so as to enable measurements to be made at the positions of the right and left femoralis, as well in the waistband area as indicated in FIG. 4. As can be seen in this Figure, a first pair of electrodes 22 in the waistband are arranged at the hip positions, where a current I1 is injected, i.e. corresponding generally to the electrodes 4 illustrated in FIG. 2, whilst a further pair of electrodes 24 also in the waistband are used for making a corresponding measurement of voltage changes V1, i.e. corresponding generally to the electrodes 6 of FIG. 2.

Further electrodes 26 and 28 are arranged respectively at the right and left leg positions, and in this way, for example, a current I2 can be injected between the corresponding waistband electrode 22 and the right leg electrode 26, to enable a voltage V2 to be measured, relative to the waistband position, at an electrode 30. Similarly, by injecting a current I3 between a left leg electrode 28 and the corresponding waistband electrode 22, a voltage V3 can be measured, relative to the waistband, at an electrode 32.

Figure 7:
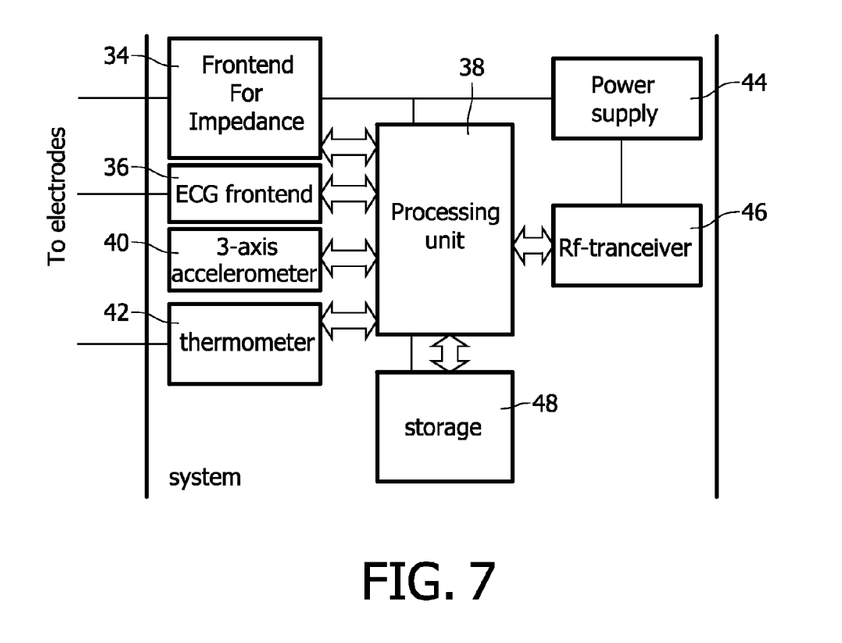
FIG. 7 is a schematic diagram of a signal processing unit.

FIG. 7 illustrates a signal processing circuit, suitable for integration into a garment as indicated at 20 in FIG. 4, which combines a number of functions in the same unit. A front-end circuit 34 for impedance and a front-end circuit 36 for ECG measurements are connected to a central processing unit 38, and in order to allow compensation to be made for patient movements as well as the detection of the patient's posture and activity, a 3 axis accelerometer 40 may also be incorporated, as well as a temperature sensing device 42.

A power supply 44, which, in an exemplary embodiment, incorporates long-life or rechargeable batteries, is provided for powering the unit, and a RF transceiver 46 enables the device to communicate data with external systems, such as a user interface. Storage means 48, for example a flash memory, is also incorporated to allow data to be stored or buffered whenever necessary. In this way the device can also be employed as a "Holter monitor" (ambulatory electrocardiography device) so as to record cardiac activity over an extended period of time.

Figure 8:
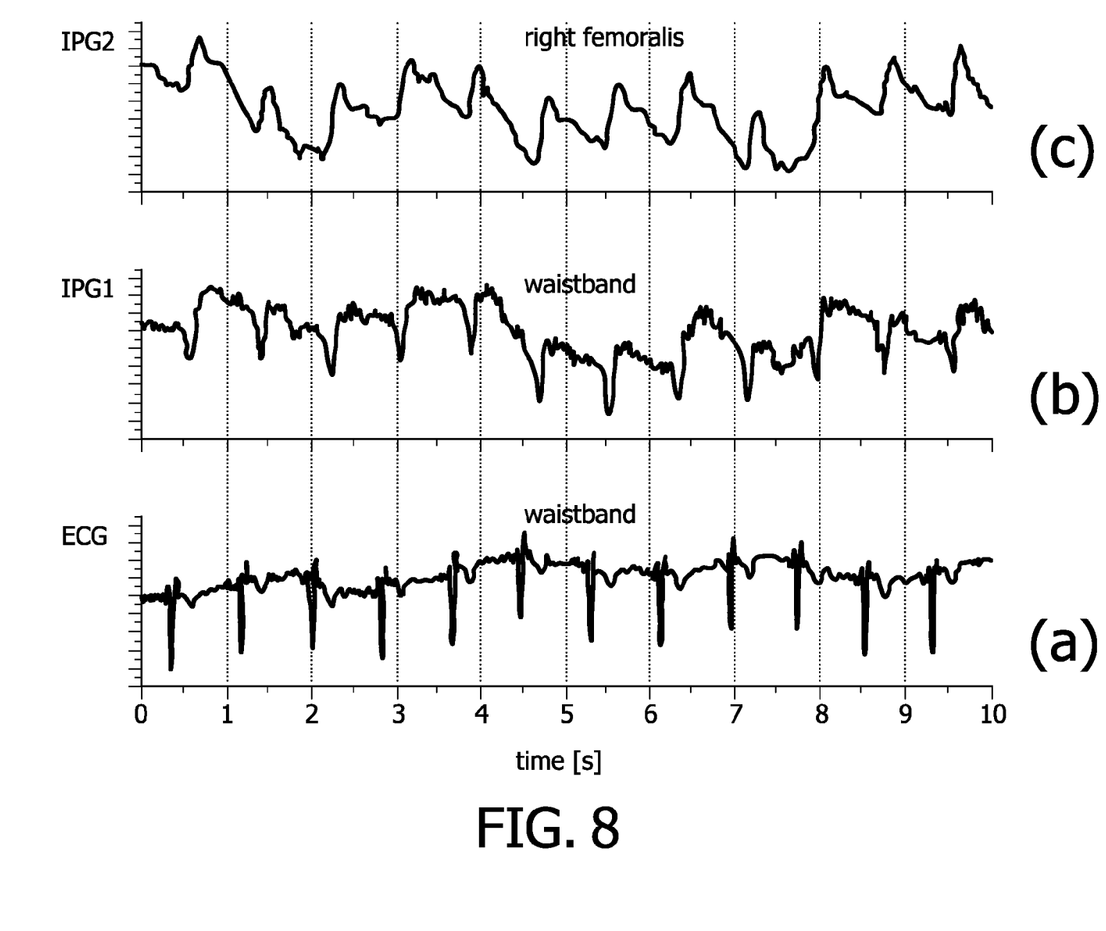
FIG. 8 illustrates ECG, IPG1, and IPG2 signals measured with the system of the invention.

FIG. 8 illustrates examples of signal measurements made with the system, in which FIG. 8(a) shows an ECG measurement taken at the waistband. Similarly, FIG. 8(b) illustrates an IPG1 (impedance plethysmogram) as measured at the waistband, and FIG. 8(c) indicates a corresponding plethysmogram IPG2 taken at the right femoralis.

Figure 9:
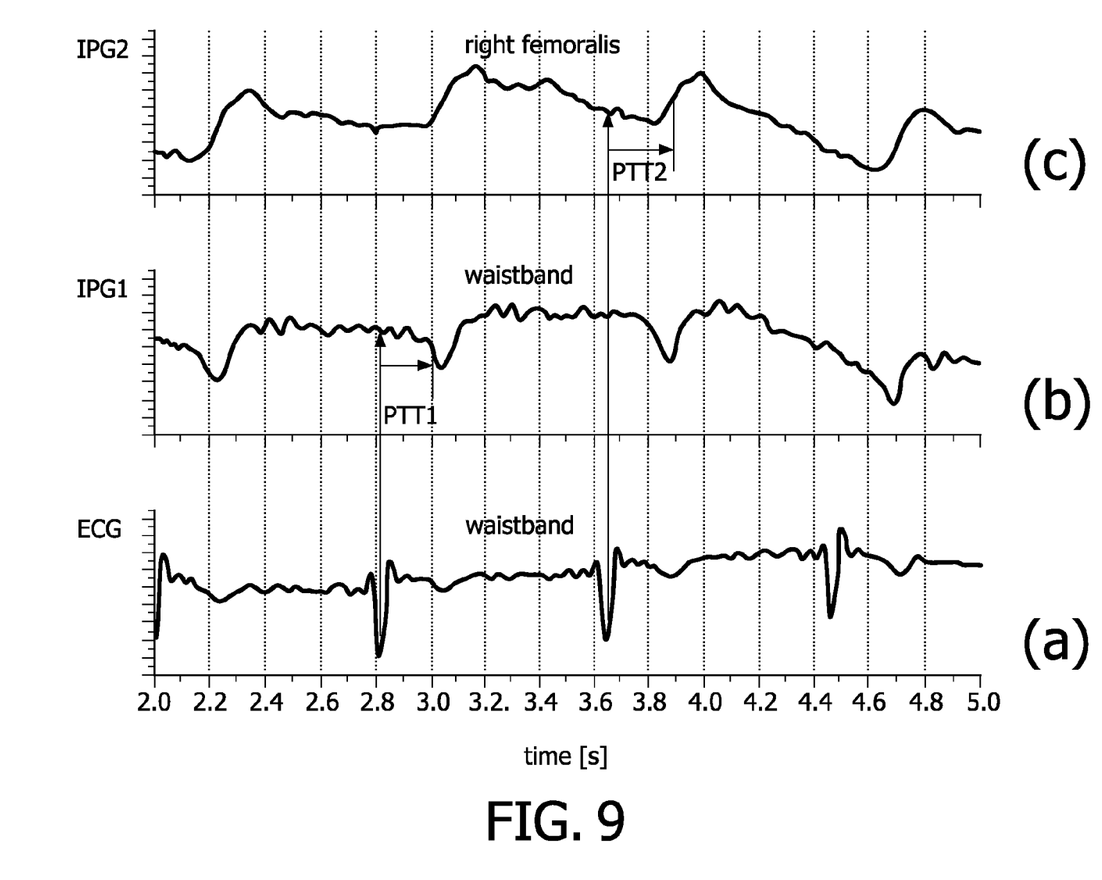
FIG. 9 is a close-up of the signals of FIG. 8.

FIG. 9 is an enlarged close-up view of the signals of FIG. 8, which shows how features can be extracted from the signals. By comparison of FIGS. 9(a) and 9(b), a pulse transit time 1, i.e. ECG to IPG1, can be derived, and by comparison of FIGS. 9(a) and 9(c), a pulse transit time PTT2, i.e. ECG to IPG2 can be also be derived.

Accordingly, it will be appreciated that the system of the invention allows the following different measurements to be taken:

Measured Signals:

The ECG of a subject, the electrical activity of the heart (no standard lead)

The blood volume pulse going into the left and right leg during a heartbeat (measured by an Impedance plethysmogram (IPG) of right and left leg), which indicates the mechanical performance of the heart activity 3 axis acceleration (static and dynamic)

Temperature

Time

Consequently the system is able to provide information on a broad portfolio of cardio-vascular parameters derived from the measured signals such as:

Heart rate

Detection of Arrhythmias 4 several Pulse transit Times (ECG->IPG1, ECG->IPG2, ECG->IPG3, IPG1->IPG2)

Arterial stiffness/Augmentation index

Relative blood pressure changes

Absolute blood pressure

Blood perfusion to left and right leg

Stroke volume

Activity measures (at rest, posture, movements)

Context information derived from these signals (time, temperature, acceleration)

Various different useful applications are therefore possible, such as:

Continuous Blood Pressure monitoring

Sleep quality detection

Hypertension Management

Blood Pressure Halter Monitoring

Elderly Care

Continuous monitoring e.g. during cardiac-rehabilitation

The invention claimed is:

1. A measuring system for measuring blood pressure of a patient, comprising:
   underpants having a waistband, a right leg portion, and a left leg portion;
   a plurality of electrodes carried by the underpants, the plurality of electrodes including one or more electrode pairs carried by the waistband, one or more electrode pairs carried by the right leg portion, and one or more electrode pairs carried by the left leg portion;
   a power supply that supplies power to the measuring system, wherein the power supply is configured to inject currents into the electrode pairs; and
   a signal processing circuit configured to receive output signals generated by the plurality of electrodes carried by the underpants to determine pulse-transit times based on the output signals received from the plurality of electrodes, wherein the output signals are indicative of voltage changes across the electrode pairs caused by the injected currents, and wherein the signal processing circuit is further configured to determine the blood pressure of the patient based on the pulse-transit times.

2. The measuring system of claim 1, wherein individual electrodes of the plurality of electrodes comprise dry electrodes of conductive rubber.

3. The measuring system of claim 1, wherein the electrodes carried by the right leg portion enable measurements of the right femoralis, wherein electrodes carried by the left leg portion enable measurements of the left femoralis, wherein the signal processing circuit determines pulse-transit times using:
   an ECG measurement based on the one or more electrode pairs carried by the waistband of the underpants; and
   an impedance plethysmography measurement based on the one or more electrode pairs carried by the right leg portion or the one or more electrode pairs carried by the left leg portion;
   and wherein the signal processing circuit is configured to determine pulse-transit times based on both the ECG measurement and the impedance plethysmography measurement.

4. The measuring system of claim 1, wherein the signal processing circuit is further configured to determine electrical activity of a heart of the patient based on measurements derived from the one or more electrode pairs carried by the waistband of the underpants.

5. The measuring system of claim 1, wherein the blood pressure is determined by applying the pulse-transit times in accordance with a Moens-Korteweg equation, wherein the pulse-transit times correspond to pulse wave velocity, and wherein the Moens-Korteweg equation equates pulse wave velocity c to the square root of the ratio of the product of artery wall thickness h and tangential elasticity E with the product of twice the density $\rho$ and artery radius R, as follows:

$$c=\sqrt{((h \cdot E)/(2 \cdot \rho \cdot R))}.$$

6. The measuring system of claim 3,
   wherein the plurality of electrodes include at least four electrodes carried by the waistband, two electrodes carried by the right leg portion, and two electrodes carried by the left leg portion, wherein a first current is injected by the power supply into a first pair of electrodes, the first pair of electrodes comprising:
      a first electrode of the electrodes carried by the waistband of the underpants, and
      a first electrode of the electrodes carried by the right leg portion;
   wherein a second current is injected by the power supply into a second pair of electrodes, the second pair of electrodes comprising:
      a second electrode of the electrodes carried by the waistband of the underpants, and
      a first electrode of the electrodes carried by the left leg portion;
   wherein a first voltage change caused by the first current is measured across a third pair of electrodes to produce the impedance plethysmography measurement, the third pair of electrodes comprising:
      a third electrode of the electrodes carried by the waistband of the underpants, and
      a second electrode of the electrodes carried by the right leg portion;
   wherein a second voltage change caused by the second current is measured across a fourth pair of electrodes to produce a second impedance plethysmography measurement, the fourth pair of electrodes comprising:
      a fourth electrode of the electrodes carried by the waistband of the underpants, and
      a second electrode of the electrodes carried by the left leg portion; and
   wherein the pulse-transit times are based on both the ECG measurement and one or both of the impedance plethysmography measurement and/or the second impedance plethysmography measurement.

7. The measuring system of claim 1, further comprising a 3-axis accelerometer whereby the system can detect the patient's posture or movements and compensate for signal artifacts caused by the patient's posture or movements.

8. The measuring system according to claim 1, wherein the signal processing circuit includes a front-end circuit for receiving sensor signals means for storing data, and rf-transceiver for communication with an external system.

9. The measuring system of claim 8, wherein the signal processing circuit is further configured to receive manual input from the patient and to transmit information, relating to the condition of the system and the condition of the patient, to the external system.

10. The measuring system of claim 9, further comprising an alarm for alerting the patient to a critical condition pertaining to the determined blood pressure of the patient.

11. The measuring system of claim 10, wherein the transmitted information with the external system includes an alert to a source of external professional assistance.

12. The measuring system of claim 8, wherein the system is arranged to operate as a Holter monitor or ambulatory electrocardiography device, so as to record cardiac activity over an extended period of time.

13. A system for measuring blood pressure of a patient, comprising:
  underpants having a waistband and a leg portion;
  a power supply to supply power for the system, wherein the power supply is configured to inject currents into electrode pairs, and wherein the power supply supplies power to perform measurements of voltage changes across electrode pairs caused by the injected currents;
  a plurality of electrodes carried by the underpants, the plurality of electrodes including at least two electrode pairs carried by the waistband and at least two electrodes carried by the leg portion; and
  a signal processing circuit configured to:
    perform an ECG measurement using a first current injected by the power supply into a first electrode pair that is carried by the waistband of the underpants, wherein output signals indicative of voltage changes caused by the first injected current are generated by a second electrode pair that is carried by the waistband of the underpants;
    perform a first impedance plethysmography measurement, wherein a second current is injected by the power supply into an electrode pair that is carried by the waistband of the underpants, wherein voltage changes caused by the injected second current are measured between an electrode pair that is carried by the waistband of the underpants;
    perform a second impedance plethysmography measurement, wherein a third current injected by the power supply into an electrode pair having at least one electrode that is carried by the leg portion, wherein voltage changes caused by the injected third current are measured between an electrode pair having at least one electrode that is carried by the leg portion;
    determine a first pulse-transit time based on the ECG measurement and the first impedance plethysmography measurement;
    determine a second pulse-transit time based on the ECG measurement and the second impedance plethysmography measurement; and
    determine the blood pressure of the patient based on the first pulse-transit time and the second pulse-transit time.

14. A system for measuring blood pressure of a patient, comprising:
  underpants having a waistband and a leg portion;
  a power supply to supply power for the system, wherein the power supply is configured to inject currents into electrode pairs, and wherein the power supply supplies power to perform measurements of voltage changes across electrode pairs caused by the injected currents;
  a plurality of electrodes carried by the underpants, the plurality of electrodes including at least two electrode pairs carried by the waistband and at least two electrodes carried by the leg portion; and
  a signal processing circuit configured to:
    perform an ECG measurement using a first current injected by the power supply into a first electrode pair that is carried by the waistband of the underpants, wherein output signals indicative of voltage changes caused by the first injected current are generated by a second electrode pair that is carried by the waistband of the underpants;
    perform an impedance plethysmography measurement, wherein a second current injected by the power supply into an electrode pair having at least one electrode that is carried by the leg portion, wherein voltage changes caused by the injected second current are measured between an electrode pair having at least one electrode that is carried by the leg portion;
    determine a pulse-transit time based on the ECG measurement and the impedance plethysmography measurement; and
    determine the blood pressure of the patient based on the pulse-transit time.

* * * * *